United States Patent [19]

Fülberth et al.

[11] Patent Number: 5,442,008

[45] Date of Patent: * Aug. 15, 1995

[54] STABILIZED POLYMER FILM COATED COMPOUNDS AND STABILIZED FORMULATIONS IN COMPRESSED FROM USING SAME

[75] Inventors: Werner Fülberth; Richard Leeb; Manfred Radau, all of Kelkheim; Willi Stammberger, Hofheim am Taunus, all of Germany

[73] Assignee: Hoechst Aktiengesellschaft, Frankfurt am Main, Germany

[ * ] Notice: The portion of the term of this patent subsequent to Sep. 29, 2009 has been disclaimed.

[21] Appl. No.: 194,634

[22] Filed: Feb. 10, 1994

Related U.S. Application Data

[63] Continuation of Ser. No. 921,757, Jul. 30, 1992, abandoned, which is a continuation of Ser. No. 274,598, Nov. 22, 1988, Pat. No. 5,151,433.

[30] Foreign Application Priority Data

Nov. 24, 1987 [DE] Germany ............... 37 39 690.0

[51] Int. Cl.⁶ .................. A61K 31/74; C07D 209/02
[52] U.S. Cl. .................................. 424/478; 424/480; 424/482; 424/483; 514/299
[58] Field of Search ................... 424/490, 480, 482

[56] References Cited

U.S. PATENT DOCUMENTS

| | | | |
|---|---|---|---|
| 3,565,559 | 2/1971 | Sato et al. | 424/37 |
| 4,344,949 | 8/1982 | Hoefle et al. | 424/258 |
| 4,374,829 | 2/1983 | Harris et al. | 424/177 |
| 4,425,355 | 1/1984 | Hoefle et al. | 424/274 |
| 4,743,450 | 5/1988 | Harris et al. | 424/440 |
| 4,808,413 | 2/1989 | Joshi et al. | 424/458 |
| 4,898,732 | 2/1990 | Fernandez | 424/422 |
| 4,919,938 | 4/1990 | Lovegrove et al. | 424/480 |

FOREIGN PATENT DOCUMENTS

| | | | |
|---|---|---|---|
| 0050800 | 5/1982 | European Pat. Off. | C07C 103/52 |
| 0079022 | 5/1983 | European Pat. Off. | C07D 209/52 |
| 0158927 | 10/1985 | European Pat. Off. | C07K 5/06 |
| 0196546 | 10/1986 | European Pat. Off. | A61J 3/10 |
| 0243645 | 11/1987 | European Pat. Off. | C07K 5/06 |
| 0288732 | 11/1988 | European Pat. Off. | . |
| 0050191 | 4/1992 | European Pat. Off. | A61K 9/28 |
| 3610391 | 10/1987 | Germany | C07D 209/42 |
| 8503436 | 8/1985 | WIPO | 424/480 |
| WO8503436 | 8/1985 | WIPO | . |

OTHER PUBLICATIONS

Chemical Abstracts, vol. 108: 62328v (Feb. 2, 1988).
International Pharmaceutical Abstracts, vol. 3 (17): 1194 (Sep. 1966).
Leo Gu et al., Pharmaceutical Research, vol. 4, No. 5 (1987) pp. 392–397.
Hagers Handbook of Pharmaceutical Practice, vol. 7A: 499–502 (Berlin 1971).
W. A. Ritschel, Die Tablette (1966).
US-Pharmacop. XXI p. 1492.
Dictionaire Vidal, pp. 1276–1277 (Paris 1986).

*Primary Examiner*—Thurman K. Page
*Assistant Examiner*—Peter F. Kulkosky
*Attorney, Agent, or Firm*—Finnegan, Henderson, Farabow, Garrett & Dunner

[57] ABSTRACT

Stabilized medicinal substances, a process for the preparation thereof, and stable medicinal formulations Stabilized compounds of the formula I

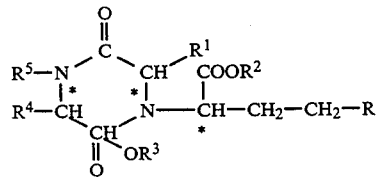

in which R, $R^1$, $R^2$, $R^3$, $R^4$ and $R^5$ have the stated meanings, and a process for the preparation thereof, are described. The stabilized compounds are suitable for the manufacture of medicinal formulations. The formula I compounds are stabilized by a polymeric protective coating before being compressed in tablet form.

16 Claims, No Drawings

STABILIZED POLYMER FILM COATED COMPOUNDS AND STABILIZED FORMULATIONS IN COMPRESSED FROM USING SAME

This application is a continuation of application Ser. No. 07/921,757, filed Jul. 30, 1992, now abandoned, which is a continuation of application Ser. No. 07/274,598, filed Nov. 22, 1988, now U.S. Pat. No. 5,151,433, issued Sep. 29, 1992.

Stabilized medicinal substances, a process for the preparation thereof, and stable medicinal formulations Compounds of the formula I

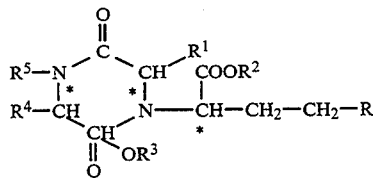

in which
R is hydrogen, $C_1$–$C_4$-alkyl or phenyl,
$R^1$ represents $C_1$–$C_4$-alkyl or

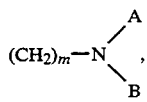

in which m is 1, 2, 3 or 4, and A and B are identical or different and denote hydrogen or $C_1$–$C_4$-alkyl,
$R^2$ is hydrogen, $C_1$–$C_4$-alkyl or benzyl,
$R^3$ is hydrogen or $C_1$–$C_4$-alkyl, and
$R^4$ and $R^5$ denote, together with the atoms carrying them, a heterocyclic, mono-, bi- or tricyclic hydrogenated or partially hydrogenated ring system which has one nitrogen atom and 4 to 15 ring carbon atoms and which is optionally mono- or disubstituted by $C_1$–$C_4$-alkoxy, represent valuable pharmaceuticals. They are, for example, inhibitors of angiotensin converting enzyme (ACE) and can be used to control high blood pressure of various etiologies. A nootropic action of these compounds has also been described (cf. German Offen-Legungsschrift 3,610,391, corresponding to EP-A 0,243,645 and U.S. patent application Ser. No. 29,905). The compounds of the formula I are disclosed in, for example, EP-A 79,022 and EP-A 50,800; in addition, reference may also be made to the citations quoted in German Offenlegungsschrift 3,610,391.

The active substances of the formula I are preferably administered orally, and solid administration forms such as, for example, tablets, coated tablets or capsules are particularly suitable.

It has been found that active substances of the formula I, such as, for example, 2-[N-[(S)-1-ethoxycarbonyl-3-phenylpropyl]-L-alanyl]-(1S,3S,5S)-2-azabicyclo[3.3.0]-octane-3-carboxylic acid (ramipril), show a tendency to be unstable in pharmaceutical formulations, depending on the auxiliaries used, the manufacturing process and the storage.

The main product of decomposition which has been detected in pharmaceutical formulations is the diketopiperazine compound produced by condensation and having the following structure II.

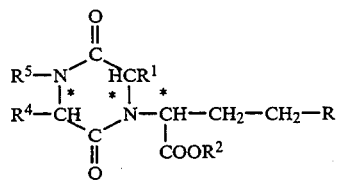

Accordingly, the main product of decomposition of ramipril is the diketopiperazine derivative of the formula IIa

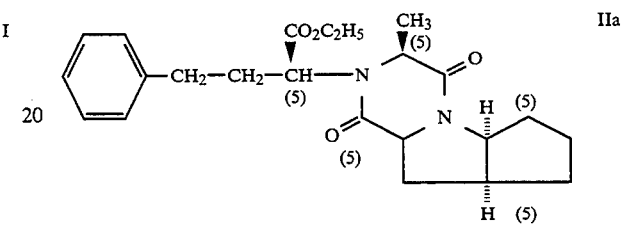

It has been found that the stability can be influenced by the choice of suitable auxiliaries, and that a significant cause of decomposition is the mechanical stress associated with the manufacturing process, especially when the active substance, for example ramipril, is present in a mixture with auxiliaries.

The investigation which is summarized in the table below illustrates the decomposition-inducing effect of the mechanical stress, taking ramipril as example.

2.5 mg ramipril tablets/effect of mechanical stress on stability.

| Diketopiperazine derivative of ramipril (%) | | | |
| --- | --- | --- | --- |
| Duration and nature of stress | 2.5 mg tablets | 2.5 mg tablets | 2.5 mg capsules |
| 3 mon. +40° C. | 13.6 | 7.6 | 4.0 |
| 6 mon. +40° C. | 22.8 | 12.0 | 6.4 |
| manufacturing process | dry granulation | direct compression | filling with the powdered mixture |
| mechanical stress | high | moderate | low |

The three formulations compared have the same composition and contain the following auxiliaries: mannitol, microcrystalline cellulose, and sodium stearylfumarate. The only difference is in the power of compression (mechan. stress) involved in the process.

The results clearly show that the mechanical stress is a significant decomposition-inducing factor.

It has also been found that the storage conditions influence the stability of the active substances of the formula I.

Decomposition is favored by increasing temperature and moisture and by the two effects of storage acting together.

The tendency of, for example, ramipril to decompose in formulations in which all the said influencing factors act together is revealed in the following comparative test:

Determinations were carried out of the contents of active substance after stress for a) the active substance itself; uncompressed
b) ramipril tablets which contained several auxiliaries and had been exposed to mechanical stress (compression):

|  | Content relative to initial value | |
|---|---|---|
| Duration and nature of stress | Ramipril active substance | Ramipril tablets |
| 6 months + 40° C. | 99% | 56% |
| 6 months + 40° C. 80% rel. hum. | 96% | <20% |

Tablets and auxiliaries used

Lactose monohydrate, corn starch, microcrystalline cellulose, sodium starch glycolate, highly disperse silica, talc and magnesium stearate.

The results clearly show that, under the chosen test conditions, the stability of the uncompressed active substance is good. Only on compression (mechan. stress) with generally used tabletting auxiliaries and after exposure to heat and, especially, moisture is there a large decrease in the content of active substance.

The preferred presentation for the active substances of the formula I is the tablet, because of the possibility of individual adjustment of the dose and better patient compliance. The presentations are, as shown by the above results, extremely unstable, especially when 1. mechanical stress (power of compression)
2. tabletting auxiliaries
3. temperature
4. moisture act together.

Whereas mechanical stresses are unavoidable in the manufacture of formulations in compressed form, attempts have been made to obtain stable formulations by changing the auxiliaries. Taking ramipril as example, it has been made possible to optimize the formula by choosing auxiliaries specifically for their compatibility with ramipril. This is illustrated by the following comparison after exposure to stress.

|  | 1 mg ramipril tablets Content relative to initial value | |
|---|---|---|
| Duration and nature of stress | Formula 1 | Formula 2 (optimized formula) |
| 6 months 40° C. Auxiliaries | 56% lactose monohydrate, maize starch, microcrystalline cellulose, Na starch glycolate, highly disperse silica, talc, magnesium stearate | 88.5% mannitol, microcrystalline cellulose, Na stearylfumarate |

However, this measure is not by itself sufficient to stabilize the tablet formulation. It has now been found, surprisingly, that a protective coating of the pure ramipril, which is prone to decompose, with polymeric film-formers counteracts the mechanical inactivation. These findings were surprising because even small amounts of coating sufficed to shield the active substance from mechanical stress.

It has additionally been found that stable tablets suitable for oral administration are obtained when the active substance of the formula I is mixed with a buffer which ensures that the pH which is set up in the formulation under the action of atmospheric humidity is in the weakly acid to weakly alkaline range (5.5 to 8.0).

Hence the invention relates to a method for the stabilization of active substances of the formula I, which comprises coating the active substance, or a mixture containing the active substance, with a polymeric protective film, or comprises mixing the active substance of the formula I with a physiologically tolerated buffer which ensures that a pH in the weakly acid to weakly alkaline range is set up in a formulation in the presence of moisture, and active substances of the formula I which have been stabilized by a polymeric protective film or by mixture with a buffer. The active substances of the formula I can be present as such or as physiologically tolerated salts.

The centers of chirality at the carbon atoms in formula I marked with an asterisk (*) preferably have the S configuration.

Active substances of the formula I in which R, $R^1$, $R^2$ and $R^3$ have the following meanings:

R: methyl or phenyl,
$R^1$: methyl or $(CH_2)_4-NH_2$,
$R^2$: hydrogen or ethyl,
$R^3$: hydrogen, and in which
$R^4$ and $R^5$ form, with the atoms carrying them, preferably the following ring systems

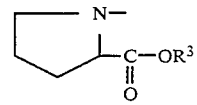

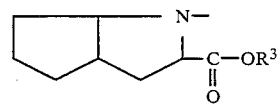

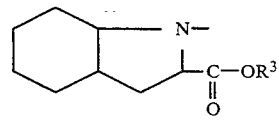

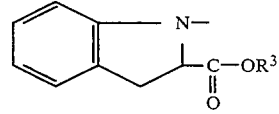

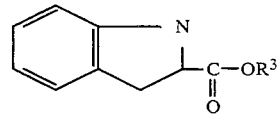

where $R^3$ is preferably hydrogen, are preferred.

Particularly suitable active substances are:
ramipril of the formula Ia

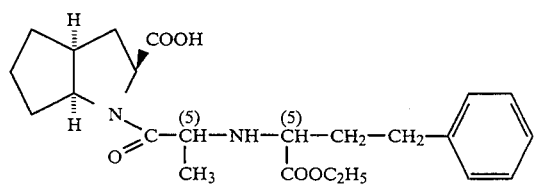

enalapril of the formula Ib

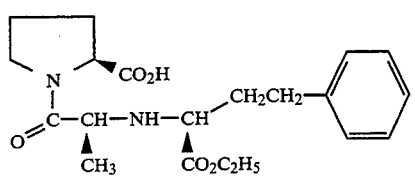

perindopril of the formula Ic

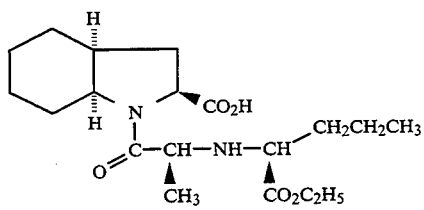

indolapril of the formula Id

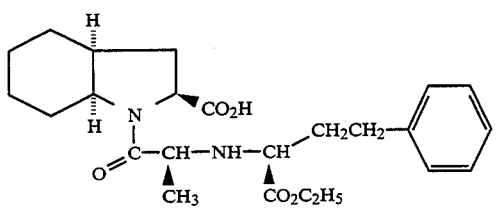

lisinopril of the formula Ie

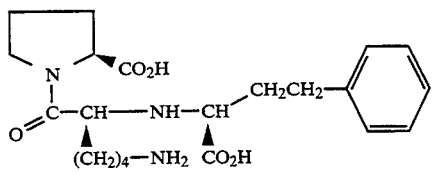

quinapril of the formula If (X=H)
alacepril of the formula If (X=3,4-OCH3)

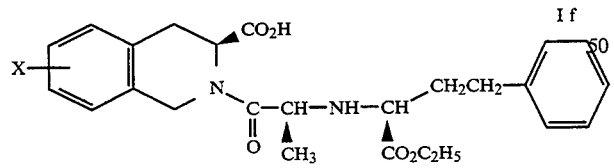

trandolapril of the formula Ig

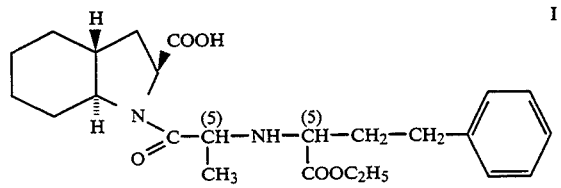

and
CGS 13928 C of the formula Ih

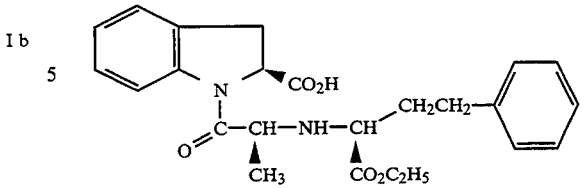

Protective coatings in concentrations of as little as 3 to 25%, preferably 5 to 15% (per cent by weight relative to the active substance which is to be coated), are effective. It was not to be expected that even thin film coatings are able to shield the contents from the high mechanical stresses customary in the tabletting process (5 KN to 30 KN).

It was additionally surprising that the polymers provided for the protective coating can be used as aqueous solutions without having an adverse effect on the stability.

EXAMPLES OF POLYMERS SUITABLE FOR THE PROTECTIVE COATING

Cellulose derivatives such as, for example, hydroxypropylcellulose, hydroxypropylmethylcellulose, hydroxypropylmethylcellulose, phthalate, hydroxyethylcellulose, ethylcellulose, cellulose acetate phthalate, cellulose acetate, polyvinyl acetate phthalate, polyvinylpyrrolidone, cationic and anionic polymers, copolymer with neutral character based on poly(meth)acrylic esters (Eudragit® E, Eudragit® E 30 D), anionic polymer of methacrylic acid and methyl methacrylate (Eudragit® L or S, Eudragit® L 30 D) and gelatin. In principle, all physiologically tolerated polymers are suitable.

The protective coating can be carried out by dispersing the active substance with the solution or dispersion of the film-former in a suitable kneader, mixer or mixer-granulator. The uniformly wetted composition is then forced through a screen and dried. The dried granules are once more passed through a screen and then used to manufacture capsules or tablets. A particularly uniform 0 coating is obtained in a fluidized bed. The particles of active substance are sprayed in the stream of air with a solution or dispersion of the polymer and are dried. The coated granules of active substance can be used immediately after the drying process for filling capsules or for manufacturing tablets.

However, it is also possible to combine the two processes together by initially wetting the active substance with the solution or dispersion of the polymer in a kneader, mixer or mixer-granulator, and subsequently processing it by granulation to give homogeneous agglomerates which are then finally coated with the solution or dispersion of the polymer in a fluidized bed.

The active substances stabilized with a protective film by the method according to the invention can be processed to give capsules or compressed administration forms. Such products are stable by comparison with products which are manufactured with untreated active substance. This is revealed best by the example of tablets in which the diminution in stability by the mechanical stress during manufacture becomes evident after subsequent exposure to heat.

A stability comparison with a standard formula without protective coating is shown in the table which follows.

TABLE 1

2.5 mg ramipril tablets
Stability comparison/stabilizing effect of a protective coating
Nature of stress: 6 months + 40° C.
Packaging: GLass tubes with tight screw closure

| Composition in mg | Standard formula | Tablets manufactured according to the invention as in Example 5 |
|---|---|---|
| uncoated pure ramipril | 2.50 | — |
| 87%* pure ramipril *contains 13% HPMC as film coating | — | 2.87 |
| microcrystalline cellulose | 47.00 | 47.00 |
| free-flowing mannitol | 49.50 | 49.13 |
| Na stearylfumarate | 1.00 | 1.00 |
| tablet weight | 100.00 | 100.00 |
| compressive force | 10,000 N | 10,000 N |
| decomposition to the diketopiperazine breakdown product in % | 12.72 | 1.87 |

Table 2 which follows demonstrates that a relatively thin coating of ramipril is still effective even after lengthy stress.

TABLE 2

2.5 mg ramipril tablets
Stability comparison
Nature of stress: 12 months + 40° C.
Packaging: Glass tubes with tight screw closure

| Composition in mg | Standard formula | Tablets manufactured according to the invention as in Example 6 |
|---|---|---|
| uncoated pure ramipril | 2.50 | — |
| 94%* pure ramipril *contains 6% HPMC as film coating | — | 2.66 |
| microcrystalline cellulose | 25.00 | 25.00 |
| free-flowing mannitol | 71.50 | 71.34 |
| Na stearylfumarate | 1.00 | 1.00 |
| tablet weight | 100.00 | 100.00 |
| compressive force during tabletting | 10,000 N | 10,000 N |
| decomposition to the diketopiperazine breakdown product in % | 25.34 | 5.97 |

On stabilization by admixture of a buffer, the latter is mixed either with the active substance or with the coated active substance, during which the active substance or the coated active substance is being granulated with a buffer solution or is present in the dispersion or solution of the polymeric substance when both types of stabilization are used simultaneously.

The pH set up in the formulation, such as, for example, tablet, in the presence of moisture, such as, for example, atmospheric humidity or water, is between 5.5 and 8.0.

Examples of suitable buffer substances are: sodium dihydrogen phosphate dihydrate, trisodium citrate dihydrate, sodium carbonate, sodium hydrogen carbonate and tris(hydroxymethyl)aminomethane.

It is advantageous if the buffer substance is used as an aqueous solution, by the active substance being either moistened uniformly in a suitable mixer, kneader or mixer-granulator and then granulated and dried, or sprayed in a fluidized bed and spray-granulated in this way. However, it is also possible to granulate a mixture of active substance and buffer substance with water in the manner described.

It has proved particularly advantageous if the stabilizing effect produced by mixture with buffer is combined with a protective coating of the particles of active substance by polymeric film-formers.

This is carried out most advantageously in such a way that the buffer substance is already dissolved in the medium intended for coating the particles and is applied together with the polymeric film-former to the surface of the active substance. The coating techniques described for coating the particles are used for this.

The stabilizing effect of buffer substances is illustrated by the comparison in the following table (Table 3).

TABLE 3

2.5 mg ramipril tablets
Stability comparison/stabilizing effect of a buffer substances
Nature of stress: 3 months + 40° C.
Packaging: Glass tubes with tight screw closure

| Composition in mg | Standard formula | Tablets manufactured according to the invention as in Example 7 |
|---|---|---|
| pure ramipril | 2.5 | 2.5 |
| tris(hydroxymethyl)-aminomethane | — | 2.5 |
| pregelatinized starch | 51.5 | 49.0 |
| microcrystalline cellulose | 45.0 | 45.0 |
| Na stearylfumarate | 1.0 | 1.0 |
| tablet weight | 100.00 | 100.00 |
| compressive force during tabletting | 10,000 N | 10,000 N |
| pH after suspending in water | 5.4 | 6.9 |
| decomposition to diketopiperazine breakdown product in % | 7.1 | 0.6 |

USE EXAMPLES

EXAMPLE 1

Preparation of stabilized pure ramipril 87 parts by weight of pure ramipril are granulated in a fluidized bed apparatus with 13 parts by weight of hydroxypropylmethylcellulose, called HPMC hereinafter, as a 5% strength aqueous solution. Examples of suitable types are Pharmacoat ® 606 or Methocel ® E5 Premium. The process takes place in two sections, in which the pure ramipril is first granulated with one half of the HPMC solution and then coated with the second half of the 5% strength aqueous HPMC solution.

The drying temperature is about 50° C. The coated pure ramipril can be mixed with auxiliaries and used to fill capsules or compressed directly, without other granulation steps, to tablets.

EXAMPLE 2

Preparation of stabilized pure ramipril 94 parts by weight of pure ramipril are dispersed in a suitable kneader, mixer or mixer-granulator with 6 parts by weight of HPMC as a 10% strength aqueous solution until a uniformly moistened composition results. The moist composition is passed through a screen with a mesh size of 1.2 mm and is then dried at about 40° C. The dried agglomerates are once more passed through a screen with a mesh size of 0.5 to 1 mm. The finished ramipril granules can be used to manufacture capsules or tablets.

EXAMPLE 3

Preparation of stabilized pure ramipril 1 part by weight of pure ramipril and 1 part by weight of tris(hydroxymethyl)aminomethane buffer substance are mixed in a suitable mixer or mixer-granulator and then moistened with sufficient purified water to produce a uniformly wetted composition.

The moist composition is granulated in the manner described in Example 2.

EXAMPLE 4

Preparation of stabilized pure ramipril 94 parts by weight of pure ramipril, 6 parts by weight of polyvinylpyrrolidone (for example Kollidon ® K25) and 18.8 parts by weight of sodium carbonate are mixed in a suitable mixer or mixer-granulator and then moistened with sufficient purified water to produce a uniformly wetted composition. The moist composition is granulated in the manner described in Example 2.

EXAMPLE 5

Manufacture of 10,000 2.5 mg ramipril tablets 28.7 g of 87% pure ramipril (contains 13% HPMC as film coating as in Example 1), 470 g of microcrystalline cellulose and 491.3 g of free-flowing mannitol are mixed. In a second step, 10 g of sodium stearylfumarate are mixed into this mixture. 1-kg of the mixture prepared in this way is compressed directly, without other granulation steps, to tablets having a final weight of 100 mg.

EXAMPLE 6

Manufacture of 10,000 2.5 mg ramipril tablets 26.6 g of 94% pure ramipril (contains 6% HPMC as film coating as in Example 2), 250 g of microcrystalline cellulose and 713.4 g of free-flowing mannitol are mixed. In a second step, 10 g of sodium stearylfumarate are mixed into this mixture. 1 kg of the mixture prepared in this way is compressed directly, without other granulation steps, to tablets having a final weight of 100 mg.

EXAMPLE 7

Manufacture of 10,000 2.5 mg ramipril tablets 50 g of 50% pure ramipril, prepared as in Example 3, 450 g of microcrystalline cellulose and 490 g of pregelatinized starch are mixed. In a second step, 10 g of sodium stearylfumarate are mixed into this mixture.

1 kg of the mixture prepared in this way is compressed directly, without other granulation steps, to tablets having a final weight of 100 mg.

EXAMPLE 8

Manufacture of 10,000 5 mg ramipril tablets 63 g of ramipril stabilized as in Example 4, 250 g of microcrystalline cellulose and 667 g of free-flowing mannitol are mixed. In a second step, 20 g of sodium stearylfumarate are mixed into this mixture.

1 kg of this mixture are compressed directly, without other granulation steps, to tablets having a final weight of 100 mg.

EXAMPLE 9

Preparation of stabilized pure enalapril 85 parts by weight of enalapril hydrogen maleate are granulated in a fluidized bed apparatus with 15 parts by weight of hydroxypropylmethylcellulose (HPMC) as a 5% strength aqueous solution in the manner indicated in Example 1. The coated pure enalapril can be mixed with auxiliaries and used to fill capsules or compressed directly, without other granulation steps, to tablets.

EXAMPLE 10

Preparation of stabilized pure enalapril 90 parts by weight of enalapril hydrogen maleate are dispersed in a suitable kneader, mixer or mixer-granulator with 10 parts by weight of HPMC as an aqueous solution until a uniformly moistened composition is produced. The moist enalapril composition is granulated in the manner described in Example 2. The finished enalapril granules with a protective coating can be used to manufacture capsules or tablets.

EXAMPLE 11

Manufacture of 10,000 2.5 mg enalapril tablets 29.4 g of 85% pure enalapril hydrogen maleate (contains 15% HPMC as film coating as in Example 9), 480 g of microcrystalline cellulose and 480.6 g of modified free-flowing starch are mixed. In a second step, 10 g of sodium stearylfumarate are mixed into this mixture. 1 kg of this mixture is compressed directly, without other granulation steps, to tablets having a final weight of 100 mg.

EXAMPLE 12

Manufacture of 10,000 10 mg enalapril tablets 111.1 g of 90% pure enalapril hydrogen maleate (contains 10% HPMC as film coating as in Example 10), 480 g of microcrystalline cellulose and 398.9 g of modified free-flowing starch are mixed. In a second step, 10 g of sodium stearylfumarate are mixed into this mixture. 1 kg of this mixture is compressed directly, without other granulation steps, to tablets having a final weight of 100 mg.

We claim:

1. A stable pharmaceutical composition in compressed form containing a compound of the formula I:

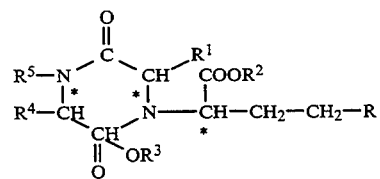

in which

R is hydrogen, $C_1$-$C_4$-alkyl or phenyl, $R^1$ represents $C_1$-$C_4$-alkyl or

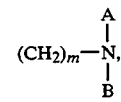

in which m is 1, 2, 3 or 4, and A and B are identical or different and denote hydrogen or $C_1$-$C_4$-alkyl, $R^2$ is hydrogen, $C_1$-$C_4$-alkyl or benzyl, $R^3$ is hydrogen or $C_1$-$C_4$-alkyl, and $R^4$ and $R^5$ denote, together with the atoms carrying them, a heterocyclic, mono-, bi- or tricyclic hydrogenated or partially hydrogenated ring system which has one nitrogen atom and 4 to 15 ring carbon atoms and which is optionally mono- or disubstituted by $C_1$-$C_4$-alkoxy, or the physiologically tolerated salts thereof, which compound is coated with a polymeric protective coating before being compressed and is substantially stabilized against decomposition to a diketopiperazine compound of formula II:

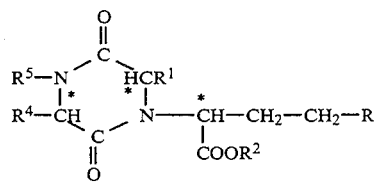

in which R, $R^1$, $R^2$, $R^4$, and $R^5$ are the same as defined for formula I, wherein the proportion by weight of the polymeric protective coating is 3 to 25% relative to said compound, and wherein said polymeric protective coating comprises a polymer selected from cellulose derivatives, polyvinyl acetate phthalate, polyvinylpyrrolidone, cationic and anionic polymers, copolymers with a neutral character based on poly(meth)acrylic esters, anionic polymers of methacrylic acid and methyl methacrylate, and gelatin.

2. Ramipril coated with a polymeric protective coating before being compressed and which is substantially stabilized against decomposition to a diketopiperazine compound of formula IIa:

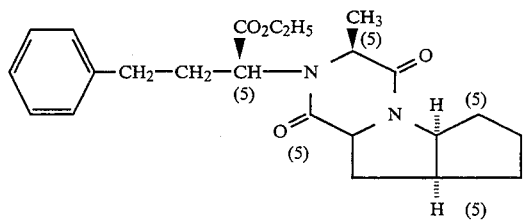

wherein the proportion by weight of the polymer protective coating is 3 to 25% relative to said ramipril and where said polymeric protective coating comprises a polymer selected from cellulose derivatives, polyvinyl acetate phthalate, polyvinylpyrrolidone, cationic and anionic polymers, copolymers with a neutral character based on poly(meth)acrylic esters, anionic polymers of methacrylic acid and methyl methacrylate, and gelatin.

3. A stable pharmaceutical composition in compressed form containing ramipril coated with a polymeric protective coating before being compressed and and substantially stabilized against decomposition to a diketopiperazine compound of formula IIa:

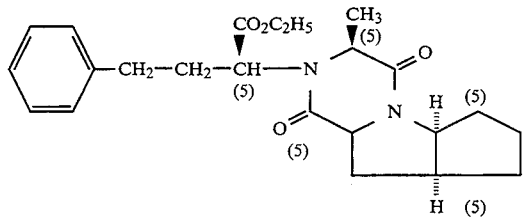

wherein the proportion by weight of the polymeric protective coating is 3 to 25% relative to said ramipril, and wherein said polymeric protective coating comprises a polymer selected from cellulose derivatives, polyvinyl acetate phthalate, polyvinylpyrrolidone, cationic and anionic polymers, copolymers with a neutral character based on poly(meth)acrylic esters, anionic polymers of methacrylic and methyl methacrylate, and gelatin.

4. The pharmaceutical composition of claim 1, wherein said coated compound is in the form of an agglomerate.

5. The ramipril of claim 2, wherein said coated ramipril is in the form of an agglomerate.

6. The pharmaceutical composition of claim 3, wherein said coated ramipril is in the form of an agglomerate.

7. A process for the preparation of the composition of claim 4, which comprises coating said compound with an amount of a polymeric protective coating sufficient so that the proportion by weight of the polymeric protective coating is 3 to 25% relative to said compound, and compressing said coated compound, wherein said polymeric protective coating comprises a polymer selected from cellulose derivatives, polyvinyl acetate phthalate, polyvinylpyrrolidone, cationic and anionic polymers, copolymers with a neutral character based on poly(meth)acrylic esters, anionic polymers of methacrylic acid and methyl methacrylate, and gelatin.

8. The composition of claim 4, wherein said polymeric protective coating comprises a cellulose derivative selected from hydroxypropylcellulose, hydroxypropylmethylcellulose, hydroxypropylmethylcellulose phthalate, hydroxyethylcellulose, ethylcellulose, cellulose acetate phthalate and cellulose acetate, 9. The composition of claim 4, wherein said polymeric protective coating comprises a polymer selected from hydroxypropylmethylcellulose and polyvinylpyrrolidone.

10. Ramipril of claim 5, wherein said polymeric protective coating comprises a cellulose derivative selected from hydroxypropylcellulose, hydroxypropylmethylcellulose, hydroxypropylmethylcellulose phthalate, hydroxyethylcellulose, ethylcellulose, cellulose acetate phthalate and cellulose acetate.

11. Ramipril of claim 5, wherein said polymeric protective coating comprises a polymer selected from hydroxypropylmethylcellulose and polyvinylpyrrolidone.

12. The process of claim 7, wherein said polymeric protective coating comprises a cellulose derivative selected from hydroxypropylcellulose, hydroxypropylmethylcellulose, hydroxypropylmethylcellulose phthalate, hydroxyethylcellulose, ethylcellulose, cellulose acetate phthalate and cellulose acetate.

13. The process of claim 7, wherein said polymeric protective coating comprises a polymer selected from hydroxypropylmethylcellulose and polyvinylpyrrolidone.

14. The composition of claim 5, wherein said polymeric protective coating comprises hydroxypropylmethylcellulose.

15. Ramipril of claim 5, wherein said polymeric protective coating comprises hydroxypropylmethylcellulose.

16. The process of claim 7, wherein said polymeric protective coating comprises hydroxypropylmethylcellulose.

* * * * *

UNITED STATES PATENT AND TRADEMARK OFFICE
CERTIFICATE OF CORRECTION

PATENT NO. : 5,442,008
DATED : August 15, 1995
INVENTOR(S) : Werner FÜLBERTH et al.

It is certified that error appears in the above-indentified patent and that said Letters Patent is hereby corrected as shown below:

Claim 3, column 11, line 53, "and substantially" should read --which is substantially--.

Claim 8, column 12, line 33, "acetate," should read --acetate.--.

Claim 14, column 12, line 57, "claim 5" should read --claim 4--.

Signed and Sealed this

Nineteenth Day of November, 1996

Attest:

BRUCE LEHMAN

*Attesting Officer*     *Commissioner of Patents and Trademarks*